(12) United States Patent
Tran

(10) Patent No.: US 6,466,045 B1
(45) Date of Patent: Oct. 15, 2002

(54) METHOD AND APPARATUS FOR TESTING A SEMICONDUCTOR PACKAGE

(75) Inventor: Dean Tran, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/636,513

(22) Filed: Aug. 10, 2000

(51) Int. Cl.[7] ............................ G01R 31/02; H04N 7/18
(52) U.S. Cl. ......................... 324/755; 324/758; 348/87
(58) Field of Search ............................... 324/755, 754, 324/758, 765, 158.1; 348/87, 94, 95

(56) References Cited

U.S. PATENT DOCUMENTS 4,677,474 A * 6/1987 Sato et al. ................... 348/87
4,929,893 A * 5/1990 Sato et al. ................... 348/87
5,105,149 A * 4/1992 Tokura ....................... 324/752

* cited by examiner

*Primary Examiner*—Ernest Karlsen

(57) ABSTRACT

Quality control during semiconductor package testing is improved and package damage in the testing apparatus is avoided by employing a camera to monitor seating of the semiconductor package in the test socket. Embodiments include linking operation of the plunger to the camera so that the plunger is activated upon proper seating of the semiconductor package in the test socket and recording semiconductor package data captured by the camera.

8 Claims, 1 Drawing Sheet

METHOD AND APPARATUS FOR TESTING A SEMICONDUCTOR PACKAGE

TECHNICAL FIELD

The present invention generally relates to the field of semiconductor manufacture, and more particularly to testing semiconductor packages in a testing apparatus.

BACKGROUND OF THE INVENTION

Quality control in the manufacturing of semiconductor packages is an increasingly important and costly aspect of the assembly process. Semiconductor package quality is controlled during the assembly process through intermediate and final product testing that assesses the physical and functional integrity of semiconductor packages.

Semiconductor package manufacturers implement intermediate testing procedures because they allow manufacturers to identify assembly errors before a final product has been made, thereby making any necessary semiconductor package rework less costly for several reasons. Intermediate testing allows manufacturers to more easily isolate where a semiconductor package assembly error occurred and the cause of the malfunction in a particular semiconductor package. For example, if a semiconductor package has only gone through solder and reflow steps, a manufacturer can determine that these assembly steps are the source of the semiconductor package malfunction before expending resources looking for problems more commonly associated with other assembly steps that have not yet occurred or that would have already been identified through prior testing procedures. Intermediate testing also reduces manufacturing costs because fewer parts are disassembled, examined and reassembled in order to identify an assembly error and repair the semiconductor package accordingly.

While intermediate testing affords manufacturers early assembly error detection, semiconductor package manufacturers also test the final semiconductor package to ensure that the fully assembled semiconductor package functions as intended. Under ideal circumstances, end-to-end testing ensures that semiconductor package manufacturers enjoy high production yields at the lowest possible cost. However, just as assembly errors leading to semiconductor package malfunction occur during or as a result of any of the assembly steps between testing procedures, testing itself can damage a semiconductor package.

In accordance with conventional testing methods, a semiconductor package is seated in a test socket comprising contacts that align with electrical leads on the semiconductor package. A plunger, controlled by a test socket control system, is then lowered to engage the test socket and semiconductor package so that the test socket can electrically communicate with the semiconductor package through the aligned contacts and electrical leads. Once testing is complete, the plunger is lifted from the semiconductor package and the semiconductor package is removed.

Testing a semiconductor package positioned in a test socket is implemented by delivering test instructions from the test socket control system to the semiconductor package and recording the results. The test data is then analyzed and the integrity of semiconductor package is assessed. Semiconductor package manufacturers identify the circumstances under which a semiconductor package ceases to properly operate under test conditions by monitoring the variants at which the computational tests fail. A semiconductor package that correctly responds to a plurality of different test instructions by generating known predetermined outputs is assessed as having good integrity.

There are several disadvantages to conventional methods of testing semiconductor packages. One disadvantage is the damage caused by the plunger when lowered onto a test socket where the semiconductor package is not properly seated. For example, it is important to ensure that the semiconductor package is facing the correct direction, e.g., face up or face down, and is oriented properly, e.g., as when components are located in a particular position relative to the semiconductor package, to complete testing. If the semiconductor package is not properly seated, the pressure from the plunger lowered onto the semiconductor package will damage the test socket and the semiconductor package. Similarly, when the plunger is lowered onto a semiconductor package that is improperly orientated on the test socket, the electrical leads of the semiconductor package are not aligned with corresponding contacts of the test socket. If the improper orientation of a semiconductor package is not realized before the plunger is lowered onto the test socket, the improperly orientated semiconductor package and the test socket will be damaged. This practice is a waste of semiconductor package manufacturer resources because of lost time associated with semiconductor package rework, lost revenue stemming from reduced production yield, and costly and time consuming test socket repair or replacement.

In addition to the physical damage that occurs when a package is not properly seated in the test socket, improper placement also triggers false test results. For example, if a semiconductor package leads do not fully connect with the test socket contacts, the test can suggest a bad semiconductor package when the real cause of the problem is improper semiconductor package seating. This error type necessitates unnecessary additional testing and/or semiconductor package rework. Conventional testing methods make it difficult to avoid these problems because they lack the ability to easily and repeatedly monitor semiconductor package seating on a test socket before and during testing to avoid initiating or continuing testing when a semiconductor package is not properly seated in a test socket.

Semiconductor package manufacturers use serial numbers to identify the make, model, manufacturing lot and other attributes for all semiconductor packages. These numbers are used, among many reasons, to direct packages through the assembly process (e.g., a certain model is processed by certain machines and not by others) and to track the source of assembly errors. Conventional testing methods do not allow manufacturers to easily identify the semiconductor package being tested. When a problem arises with a semiconductor package, or when it is otherwise necessary to identify the specific semiconductor being tested by make, model or lot, an employee must stop the testing process, go over to the testing apparatus, look at the package and record the serial numbers, thereby slowing production and increasing costs due to the inefficient use of resources. Additional errors occur when the data that is recorded is inaccurate or incomplete, thus causing a manufacturer to attribute semiconductor package malfunctions to the wrong make, model or lot and to make incorrect decisions concerning the cause and effect of such malfunctions.

There exists a need for the ability to monitor and identify semiconductor packages in a testing apparatus in preparation for and during testing procedures.

SUMMARY OF THE INVENTION

The present invention provides an apparatus for testing semiconductor packages having a plunger, a test socket configured to seat a semiconductor package, a camera for detecting semiconductor package seating and for reading and recording package-identifying information and a monitoring device. The camera is attached above the test socket so as to have an unobstructed view of a semiconductor package seated in the test socket. The monitoring device, which is attached to the camera, determines whether a semiconductor package is properly seated in the test socket based on image data generated by the camera. When a semiconductor is improperly seated in the test socket, a signal is generated that prevents the plunger from lowering onto the improperly seated semiconductor package to initiate testing.

The present invention advantageously reduces damage to the semiconductor package and testing equipment associated with conventional testing methods when testing is initiated on a semiconductor package that is not properly seated in the test socket, thereby reducing the costs associated with discarded semiconductor packages, unnecessary semiconductor package rework, equipment repair and replacement, and repetitive semiconductor package testing.

Another advantage of the present invention is the ability to view and record information located on a semiconductor package, e.g., make, model, batch, lot or other production-related data, thereby increasing production efficiencies by allowing semiconductor package manufacturers to direct packages through the assembly process after testing based on package-specific information. Additionally, a manufacturer's ability to use an embodiment of the present invention to accurately and completely capture test, performance and damage data for a particular semiconductor package enables the manufacturer to attribute semiconductor package errors and malfunctions to the correct make, model, batch or lot and to make correct decisions concerning the cause and effect of such errors or malfunctions.

The present invention also provides a method for testing semiconductor packages. The method includes the steps of placing a semiconductor package in a test socket of a testing apparatus and determining whether the semiconductor package is properly seated in the test socket in preparation for and during testing. An image is captured of the position of a semiconductor package in the test socket to detect whether the package is properly seated in the test socket. A determination is made about the semiconductor package seating, whereby a semiconductor package is determined to be improperly seated in the test socket when the image data reveals a semiconductor package not seated in the test socket according to predetermined seating parameters and properly seated when the image data reveals a semiconductor package seated according to predetermined seating parameters, e.g., semiconductor package orientation relative to the test socket, horizontal and vertical semiconductor package positioning within the test socket, alignment between the test socket contacts and semiconductor package leads, or other seating indicators. A signal is generated when the monitoring device determines that a semiconductor package is improperly seated and the test plunger is inactivated, thereby stopping test initiation. In response to a determination that a semiconductor package is properly seated in the test socket, a signal is generated that activates the test plunger and initiates testing.

The present invention advantageously improves production quality control due to fewer damaged semiconductor packages and test sockets. The manufacturing process is also simplified by reducing or eliminating the amount of semiconductor rework and testing oversight that a semiconductor manufacturer must conduct to achieve production output targets. The ability to identify and easily record data relating to semiconductor package make, model, batch or lot beneficially increases semiconductor package error detection and repair rates and also improves control over semiconductor package routing between testing and other assembly steps.

Other advantages of the present invention will become readily apparent to those skilled in the art from the following detailed description. The embodiment shown and described provides illustration of the best mode contemplated for carrying out the invention. The invention is capable of modification in various obvious respects, all without departing from the invention. Accordingly, the drawing is to be regarded as illustrative in nature, and not as restrictive.

BRIEF DESCRIPTION OF THE DRAWINGS

Reference is made to the attached drawing, wherein elements having the same reference numeral designations represent like elements throughout.

DETAILED DESCRIPTION

Figure 1:
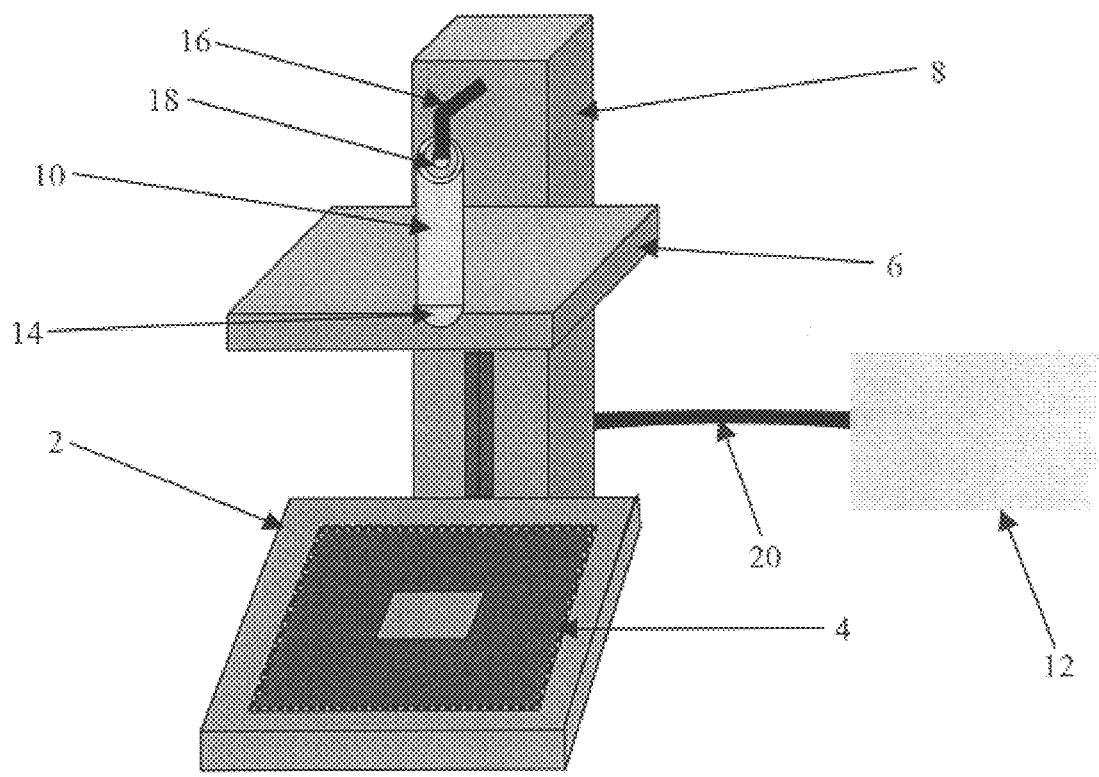
FIG. 1 shows an embodiment of the present invention comprising an apparatus for testing semiconductor packages, having a test plunger, a test socket, a camera and a monitoring device.

The present invention addresses and solves problems related to testing semiconductor packages. More specifically, it reduces semiconductor package and testing equipment damage common with conventional testing methods when testing is initiated on a semiconductor package that is improperly seated in the test apparatus. It also reduces data collection and semiconductor package routing errors stemming from the inability of manufacturers to accurately and completely read identifying information on semiconductor packages. These benefits over conventional testing methods are achieved by the monitoring and recording capabilities of the present invention.

Embodiments of the present invention comprise a testing apparatus having a plunger, a test socket configured to seat a semiconductor package, a camera for detecting semiconductor package seating and for reading and recording semiconductor package-identifying information, and a monitoring device. The camera is attached above the test socket so as to have an unobstructed view of a semiconductor seated in the test socket. The monitoring device, which is attached to the camera, determines whether a semiconductor package is properly seated in the test socket based on image data generated by the camera. When a semiconductor package is properly seated in the test socket, a signal is generated that activates the plunger and initiates testing. When a semiconductor package is improperly seated in the test socket, a signal is generated that prevents the plunger from lowering onto the improperly seated semiconductor package to initiate testing. An embodiment of the present invention is schematically illustrated in FIG. 1, wherein similar features bear similar references.

FIG. 1 shows an apparatus for testing a semiconductor package 4, the apparatus comprising a test socket 2, a plunger 6, a plunger shaft 8, a camera 10, and a monitoring device 12. The test socket 2 is configured to seat a semiconductor package 4, thereby holding the semiconductor package 4 in place in the testing apparatus during testing. The monitoring device 12 is configured to determine whether a semiconductor package 4 is properly seated in the test socket 2.

In an embodiment of the present invention, the camera 10 used to monitor semiconductor package 4 seating is an image capturing camera. It will be appreciated by one skilled in the art that the present invention can be practiced with various camera types, e.g., digital or video cameras. The camera 10 and its components also can be adapted to accommodate different testing configurations and environmental factors. For example, the lenses, filters, and film used with the camera 10 are dictated by the size of the semiconductor package 4 being tested, the light intensity in the test socket 2 area and the type of data being captured or collected by the camera 10.

The plunger 6 is attached to the plunger shaft 8 in an embodiment of the present invention. The camera 10 is attached to the plunger shaft 8 above the plunger 6 with the camera lens 14 oriented downwardly, thereby directing the camera lens 14 towards the test socket 2 area.

In an embodiment of the present invention, the camera 10 is attached to the plunger shaft 8 via an adjustable arm 16, thereby beneficially enabling variable camera 10 positioning in relation to the plunger shaft 8 and test socket 2. The camera 10 is attached to the adjustable arm 16 with a fixture 18 that rotates, pivots or otherwise moves about the adjustable arm 16, thus permitting the camera 10 to be directed at different angles or locations in the test socket 2 area and required to monitor and detect a semiconductor package's 4 position in the test socket 2 and to capture semiconductor package 4 identification information. It will be appreciated that the camera 10 is attached to the adjustable arm 16 through commonly found joint fixtures that allow the camera 10 to be pointed, as by rotating, swiveling or pivoting, in different directions, e.g., a ball and socket combination. The position of the camera 10 and adjustable arm 16 may be set or altered manually or automatically. The adjustable arm 16 is extendable beyond the plunger 6 so that the camera lens 14 has an unobstructed view of the test socket 2 and semiconductor package 4 seated therein.

An embodiment of the present invention includes a monitoring device 12, comprising a computer containing a software program for controlling plunger 6 activation and semiconductor package 4 testing. A connection 20 runs between the camera 10 and the monitoring device 12 for carrying imaging, signaling and other data between the camera 10 and the monitoring device 12. Signal transmission over the connection 20 may be duplex, half duplex or simplex. An embodiment of the present invention includes an electrical connection 20 made from a material, e.g., coaxial or fiber optic cable. The connection 20 of the present invention may comprise one or more materials. Wireless technology, e.g., infrared or other radio frequency transmission technologies may also form the connection 20. It will be appreciated that other ways suitable for carrying imaging, signaling or other data can be used to form the connection 20.

Another aspect of the present invention provides a method for testing semiconductor packages. The method includes the steps of placing a semiconductor package in a test socket of a testing apparatus and monitoring the position of the semiconductor package to determine whether it is seated properly in the test socket.

In accordance with an embodiment of the present invention, semiconductor package seating is monitored by positioning an image capturing camera over the semiconductor package seated in the test socket. The camera lens is directed towards the semiconductor package and test socket area. The camera is then activated. It will be appreciated by one skilled in the art that camera positioning and activation may be accomplished manually or automatically. Upon activation, the camera captures an image of the position and orientation of the semiconductor package in the test socket. The image data indicating the position and orientation of the semiconductor package in the test socket is transmitted to the monitoring device.

The monitoring device receives the image data indicating the position and orientation of the semiconductor package and then makes a determination whether the semiconductor package is seated in conformance with predetermined positioning and orientation parameters. For example, to complete testing, the monitoring device determines whether the semiconductor package is facing the correct direction, e.g., face up or face down, whether the semiconductor package is seated according to horizontal and vertical planar parameters within the test socket, whether there is alignment between the test socket contacts and semiconductor package leads and whether the semiconductor package is oriented properly, e.g., as when components are located in a particular position relative to the semiconductor package. This monitoring ability advantageously reduces incidents of damage to semiconductor packages and testing equipment caused with conventional testing methods when testing is initiated on an improperly placed semiconductor package and avoids false test results.

The monitoring device activates the plunger upon determining that the semiconductor package is seated in conformance with predetermined positioning and orientation parameters, thereby allowing the plunger to be lowered onto the semiconductor package seated in the test socket and initiating testing.

Upon determining that the semiconductor package is not seated in conformance with predetermined positioning and orientation parameters, the monitoring device deactivates the plunger, thereby delaying testing until the semiconductor package seating is corrected. The ability to control plunger activation until a semiconductor package is properly seated beneficially increases production yield and reduces productions costs compared with conventional testing methods by avoiding unnecessary semiconductor package damage and rework, as well as testing equipment repair and replacement.

In addition to monitoring semiconductor seating in the test socket, in an embodiment of the present invention, the monitoring device directs the camera to capture an image of the alphanumeric characters, e.g., make, model, batch, lot or other characters on the semiconductor package seated in the test socket. The camera then captures the image of the alphanumeric characters on the semiconductor package seated in the test socket and transmits the image data of the alphanumeric characters to the monitoring device. The monitoring device records the image data of the alphanumeric characters. The captured and recorded alphanumeric characters associated with a semiconductor package are used to direct packages through the assembly steps following testing, e.g., different semiconductor package models are directed to different downstream assembly steps, thereby improving production speeds and reducing manufacturer oversight associated with conventional testing methods.

The ability to electronically capture and record semiconductor package information also eliminates errors associated with manual data recording, thereby increasing the accuracy of the information used to correlate testing, performance and damage data with a particular semiconductor package and enabling the manufacturer to attribute semiconductor package errors and malfunctions to the correct make, model, batch or lot and to make correct decisions concerning the cause and effect of such errors or malfunctions.

The present invention enjoys industrial applicability in manufacturing various types of semiconductor devices and/or packages. The present invention has particular applicability in detecting and monitoring semiconductor package seating in testing equipment in preparation for and during semiconductor package testing.

Only the preferred embodiment of the present invention and but a few examples of its versatility are shown and described in the present disclosure. It is to be understood that the present invention is capable of use in various other combinations and environments and is capable of changes and modifications within the scope of the inventive concept as expressed herein.

What is claimed is:

1. An apparatus for testing a semiconductor package, the apparatus comprising:
    a test socket configured to seat a semiconductor package therein;
    a plunger;
    a plunger shaft;
    a camera positioned to capture an image of the package; and
    a monitoring device configured to: receive the captured image from the camera; determine whether a semiconductor package is properly seated in the test socket; and send a signal to activate the plunger upon determining that the package is properly seated in the test pocket or send a signal to deactivate the plunger upon determining that the package is not properly seated in the test socket.

2. The apparatus according to claim 1, wherein the camera is an image capturing camera.

3. The apparatus according to claim 2, wherein the plunger is attached to the plunger shaft.

4. The apparatus according to claim 3, wherein the camera is attached to the plunger shaft above the plunger with the camera lens oriented downwardly.

5. The apparatus according to claim 4, wherein the camera is attached to the plunger shaft via an adjustable arm.

6. The apparatus according to claim 5, wherein the camera is attached to the adjustable arm with a fixture that enables the camera to rotate, swivel or pivot about the adjustable arm.

7. The apparatus according to claim 5, wherein the adjustable arm is extendable beyond the plunger so that the camera lens has an unobstructed view of the test socket and semiconductor packaged seated therein.

8. The apparatus according to claim 7, wherein the monitoring device includes:
    a computer containing a software program for controlling plunger activation; and
    an electrical connection between the camera and testing apparatus for carrying imaging data generated by the camera to the testing apparatus for processing by the software program.

* * * * *